United States Patent [19]
Burress

[11] 3,975,300
[45] Aug. 17, 1976

[54] ONE STEP METHOD OF PREPARATION OF VANADIUM-PHOSPHORUS COMPLEX IN THE ABSENCE OF HYDROGEN HALIDE

[75] Inventor: George T. Burress, Somerville, N.J.

[73] Assignee: Mobil Oil Corporation, New York, N.Y.

[22] Filed: July 1, 1974

[21] Appl. No.: 484,491

[52] U.S. Cl. .............................. 252/435; 252/437
[51] Int. Cl.² .................................... B01J 27/14
[58] Field of Search ........................... 252/435, 437

[56] References Cited
UNITED STATES PATENTS

| | | | |
|---|---|---|---|
| 2,773,838 | 12/1956 | Reid et al. | 252/437 |
| 3,156,705 | 11/1964 | Kerr | 252/437 X |
| 3,156,706 | 11/1964 | Kerr | 252/437 X |
| 3,255,211 | 6/1966 | Kerr | 252/437 X |
| 3,255,212 | 6/1966 | Kerr | 252/437 X |
| 3,255,213 | 6/1966 | Kerr | 252/437 X |
| 3,293,268 | 12/1966 | Bergman et al. | 252/437 X |
| 3,351,565 | 11/1967 | Kerr | 252/437 |
| 3,385,796 | 5/1968 | Kerr | 252/435 X |
| 3,478,063 | 11/1969 | Friedrichsen et al. | 252/435 X |
| 3,484,384 | 12/1969 | Kerr | 252/437 |

OTHER PUBLICATIONS

United States Published Patent Application, Under Trail Voluntary Protest Program, B330,354 Jan. 28, 1975, Mount et al.

*Primary Examiner*—Patrick P. Garvin
*Assistant Examiner*—William G. Wright
*Attorney, Agent, or Firm*—Charles A. Huggett; Hastings S. Trigg

[57] ABSTRACT

V-P complex catalysts and metal promoted V-P complex catalysts having high activity and selectivity and good physical strength for the oxidation of alkenes, alkanes, cycloalkanes and mixtures rich in them to dicarboxylic acid anhydrides (e.g. maleic anhydride) are prepared by forming a paste of a vanadium compound (vanadium pentoxide), an organic reducing agent, a promoter metal salt or compound (if used), and phosphoric acid; and drying paste.

8 Claims, No Drawings

ONE STEP METHOD OF PREPARATION OF VANADIUM-PHOSPHORUS COMPLEX IN THE ABSENCE OF HYDROGEN HALIDE

BACKGROUND OF THE INVENTION

1. Field of the Invention

This invention is concerned with a one-step method for preparing vanadium-phosphorus catalysts with high activity and selectivity and good physical strength for the oxidation of alkenes, alkanes, cycloalkanes and mixtures rich therein to dicarboxylic acid anhydrides, particularly butane or butene to maleic anhydride.

2. Description of the Prior Art

Vanadium-phosphorus complex catalysts for the oxidation of butene to maleic anhydride, are described in U.S. Pat. No. 3,293,268. Such catalysts operate at temperatures greater than 500°C. In general, yields of maleic anhydride with such catalysts are relatively low and not commercially attractive or feasible.

Metal-promoted vanadium-phosphorus complex catalysts are described in U.S. Pat. No. 3,156,705. The metal promoters, identified as phosphorus stabilizers, are broadly disclosed to include transition metals and rare earth metals. The catalysts are taught for oxidizing an olefin (butene) to a dicarboxylic acid anhydride (maleic anhydride). Further, the catalysts described in this patent involve the use of a closed reflux system during their preparation, as compared to the simple open system used in this invention.

In application Ser No. 261.030, filed June 8, 1972, and continuation-in-part thereof Ser. Nos. 379,667 and 461,777 filed, respectively, July 16, 1973 and Apr. 17, 1974 there is described an improved process for oxidizing an alkane to a dicarboxylic acid anhydride in the presence of a catalyst comprising a complex reaction product of a vanadium oxysalt and phosphoric acid promoted with one or more Cr, Fe, Hf, Zr, La and Ce. The atomic ratio of P/V is between about 0.5 and about 2, and the atomic ratio of promoter metal/V is between about 0.0025 and about 1, in such catalysts. Ser. Nos. 261,030 and 379,667 are now abandoned and Ser. No. 461,777 is now U.S. Pat. No. 3,888,886.

As an improvement over, and an extension of, the catalysts described in said applications and in U.S. Pat. Nos. 3,156,705 and 3,293,268 the present invention is concerned with a simple, one-step method for making V-P catalysts. In prior catalyst preparation methods using HCl, at least 5 moles or more of HCl were required per gram atom of vanadium. Such preparation methods present a corrosivity problem requiring the use of expensive corrosion resistant equipment. They also increase the volume of material that must be handled and involve the use of closed reflux systems. The method of this invention, however, does not involve the use of hydrogen halide (HCl) and eliminates problems associated with its use. It also eliminates the need to handle large volumes of liquid and the use of a closed reflux system. When the vanadium source is a halogen-containing vanadium salt, the amount of by-product hydrogen halide encountered is comparatively small and involves a relatively negligible problem.

SUMMARY OF THE INVENTION

In accordance with the present invention, there is provided a one-step method for preparing vanadium-phosphorus composites which are catalytically active and selective for the oxidation of an alkene, alkane, cycloalkane or mixtures thereof to a dicarboxylic acid anhydride and which have high physical strength. The method comprises forming a paste (1) of a vanadium compound, an oganic reducing agent, and phosphoric acid or a compound which hydrolyzes to phosphoric acid or (2) of a vanadium compound, an organic reducing agent, a promoter metal salt or compound and phosphoric acid or a compound which hydrolyzes to phosphoric acid; and drying the paste.

The invention is also concerned with a process for oxidizing an alkene, alkane, cycloalkane or mixtures rich in them to a dicarboxylic acid anhydride by contacting them with a molecular oxygen-containing gas under specified conditions in the presence of said composites.

DESCRIPTION OF SPECIFIC EMBODIMENTS

The catalysts produced by the method of this invention are effective in the oxidation of alkenes, alkanes, cycloalkanes, and mixtures rich in alkanes and cycloalkanes to maleic anhydride in good yields and with good selectivity. Many of these catalysts also have the high physical strength needed to be used in fluid bed reactors.

In accordance with this invention, the catalysts are produced by mixing a vanadium compound, (if used) a promoter metal compound, an organic reducing agent, and phosphoric acid to form a paste. Water can be used in amounts beween about 0 weight percent and about 50 weight per cent of the total weight of solids. The water is conveniently introduced via a solution of promoter metal salt therein. Mixing can be effected, generally at room temperature, in any manner, such as manually or on mechanical mixing equipment, e.g., kneading machines and homogenizers.

Vanadium compounds employable herein are $V_2O_5$, $VOCL_3$, $VO(NO_3)_3$, $NH_4VO_3$ and $VF_5$, of which $V_2O_5$ is particularly preferred.

It is contemplated that any organic reducing agent can be used in the method of this invention. It is preferred to use hydroxy- or oxo-compound including hydroxy- or oxo-alkanoic acids having 2–3 carbon atoms, such as glycolic acid, glyoxylic acid, pyruvic acid, and lactic acid; glycols, such as ethylene glycol, propylene glycol, the polyalkylene glycols; sugars, such as fructose, sucrose, maltose, and lactose; or mixtures of reducing agents, such as ethylene glycol and sucrose. The amount of reducing agent used will be about one equivalent per atom of vanadium, although slightly more or less can be used.

The catalyst preparation method of this invention is broadly applicable to the preparation of any vanadium-phosphorus-oxygen complex oxidation catalyst. Thus, it can be used to prepare V-P-O catalysts, such as those defined in U.S. Pat. No. 3,293,268 to which reference is made. It is also contemplated for preparing promoted or "stabilized" V-P-O catalysts, such as those described in U.S. Pat. No. 3,156,705 to which reference is made. Promoted V-P-O catalysts found useful in oxidizing saturated hydrocarbons, as set forth in the aforementioned Ser. No. 261,030, are those in which the promoter metal is Cr, Fe, Hf, Zr, La or Ce. Iron and hafnium are particularly useful in fixed bed operations, while zirconium is preferred for fluid bed operations.

Accordingly, the promoter metal used in the promoted V-P-O complex catalysts are arsenic, chromium, the rare earth elements, and metals from Groups Ib, IIb, IIIa, IIIb, IVa, IVb, Va, and metals in the fourth period of Group VIII. These groups are based upon the Periodic Chart of the Elements published in Lange's Handbook of Chemistry, pages 60 and 61, Tenth Edition 1967. Preferred metals are copper, silver, zinc, cadmium, aluminum, gallium, indium, scandium, yttrium lanthanum, germanium, tin, lead, titanium, zirconium, halnium, antimony, bismuth, arsenic, iron, cobalt, nickel, cerium, praseodymiun, heodymium, and chromium. The promoter metal is introduced into the paste in the form of a compound of the promoter metal, such as nitrate, chloride, acetate, oxalate, oxide, carbonate, and the like. Preferably, the promoter metal compound is water-soluble and is incorporated into the paste as an aqueous solution, as indicated hereinbefore.

The quantity of promoter me;tal compound employed is from about 0.0025 to about 0.5 gram atom per gram atom of vanadium compound. Thus, the quantities of vanadium compound and promoter metal compound are such that the atomic ratio of promoter metal/V of the final composite is between about 0.0025 and about 0.5, preferably between about 0.005 and about 0.5.

The phosphorus/vanadium atomic ratio can be about 0.5 – 2.0/1. Accordingly, there will be used between about 0.05 gram atom and about 2.0 gram atoms of phosphoric acid or compound hydrolyzable thereto per gram atom of vanadium compound. A P/V atomic ratio of about 1.2/1 is preferred.

After it is formed, the paste is evaporated to substantially dry condition by any suitable means, such as in trays, by spray drying at 110° – 150°C., etc. The dried material is ground to about 20 – 60 mesh (U.S. Sieve Series) for fixed bed operation. The ground material can be pelletized, for example, to ⅛ inch × 5/32 inch cylindrical pellets. Optionally, a binder such as stearic acid, can be added before pelletizing. The paste can also be extruded and pelletized before drying and then dried to form catalyst pellets suitable for fixed bed operation. Alternatively, the catalyst paste, before drying, can be used to impregnate a suitable carrier such as alumina, alundum, silica, silicon carbide, silica-alumina, zirconium phosphate, and/or a zeolite, to produce a supported catalyst suitable for use in a fixed or fluidized bed reactor. As a further and preferred alternative, the dried, unsupported catalyst can be ground to produce a powdered catalyst (e.g., 60 – 200 mesh) for use in a fluidized bed reactor.

The catalyst can be conditioned in the reactor by passing a hydrocarbon-air mixture through the catalyst bed at about 450°C., prior to running the oxidation reaction. Such conditioning is, however, not necessary to obtain catalyst efficiency. In practice, anhydride product can be obtained upon commencing the flow of oxidation feed through the reactor.

The charge stocks utilizable in the process using the catalyst of this invention are alkanes having between 4 to 6 carbon atoms, alkanes having between 4 and 10 carbon atoms, cycloalkanes having between 4 and 10 carbon atoms, or mixtures of hydrocarbons rich in alkanes and cycloalkanes having between 4 and 10 carbon atoms and/or alkenes.

Typical alkenes are butene-1, butene-2 (cis or trans), 3-methylbutene-1, pentene-1, pentene-2, hexene-1, 3,3-dimethylbutene-1, and 3-methylpentene-2. It is also contemplated to use refinery streams rich in alkenes, particularly streams containing 70 percent or more butenes. The alkanes can be normal alkanes or they can have branching. Typical alkanes are butane, pentane, isopentane, hexane, 3-methylpentane, heptane, octane, isooctane, and decane. The cycloalkanes utilizable can be methyl substituted and include cyclobutane, cyclopentane, methylcyclopentane, cyclohexane, methylcyclohexane, 1,4-dimethylcyclohexane, cycloheptane and cyclooctane. Mixtures of hydrocarbons rich in alkanes and cycloalkanes having between 4 and 10 carbon atoms, i.e., containing about 70 weight percent or more alkanes and cycloalkanes, are well known in the art. Particularly suitable and readily available mixtures are naphthas obtained from paraffinic or naphthenic petroleum sources. Full boiling range naphthas (boiling within the range of about 35 – 230°C.) can be used but it is preferred to use light naphtha cuts boiling within the range of about 35° – 145°C. The naphthas usually contain about 5 – 15 percent benzene and alkylbenzenes. It has been found that benzene is oxidized to maleic anhydride, whereas to some extent alkylbenzenes are oxidized to benzene carboxylic acids or phthalic anhydride. It will be understood that other mixtures can be used, such as a paraffinic raffinate from the glycol-water solvent extraction of reformates (Udex process).

Butane, because of its ready availability, is preferred. In the following discussion and exemplification, therefore, butane is used in most examples to demonstrate (but not to limit) the use of the catalysts made by the process of this invention for producing maleic anhydride. It is contemplated that mixtures rich in butane can be used, such as a typical butane-butene (B-B) refinery stream.

The oxidation of n-butane (or other feed as aforedefined) to maleic anhydride is carried out using air or other molecular oxygen-containing gases, such as mixtures of carbon dioxide and oxygen or mixtures of nitrogen or steam with air or oxygen. Air is preferred. The oxidation reaction is carried out at temperatures of 300° – 600°C., preferably 325° – 550°C. The feed concentration is 0.5 – 6 volume percent hydrocarbon in the oxygen-containing gas and preferably 1 – 5 volume percent. The contact time is generally varied between about 0.08 – 3 seconds, preferably about 0.16 – 1.6 seconds for fixed bed operation. Generally, contact time of up to about 30 seconds can be used in the case of fluidized bed operation. Thus, contact time, depending upon the type of operation, will be about 0.08 – 30 seconds. Although the reaction can be carried out at 0.5 – 20 atmospheres pressure (absolute), it is preferably carried out at about 1 – 5 atmospheres.

The reaction can be carried out in any suitable reactor for effecting vapor phase oxidation reactions. For example, a fixed catalyst bed can be employed. The reaction can be carried out, preferably by using smaller catalyst particles in a fluidized reactor bed.

In the examples and tables, percent yield of "MA" indicates maleic anhydride yield expressed as weight of desired product bases upon weight of (butane) feed (wt. %) and was determined by titration.

Similarly, selectivity to maleic anhydride is represented by:

$$\frac{\text{moles of maleic anhydride product}}{\text{moles of hydrocarbon feed reacted}} \times 100$$

Contact time is determined by:

quiescent catalyst bed volume

The flow rates of air and butane were measured at room temperature and pressure.

The attrition index (A.I.) is a relative rating of the percent fines produced from the catalyst under test compared to the fines produced from a commercial vanadium sulfate (about 3%) on silica gel catalyst (Grace No. 906) used in a fluid process for oxidizing naphthalene to phthalic anhydride. The percent fines is determined in 1 inch I.D. copper tube fluid bed apparatus provided at the top with a disengaging section adapted to retain particles of 40 microns or greater in diameter and provided with a thimble to entrap smaller size particles, i.e., fines. In operation, a weighed sample (about 20 ml.) of catalyst is placed in the fluid bed apparatus and the thimble is tared. Air is passed upwardly through the bottom of the tube at a rate of 13 liters per minute. After one hour, the air flow is stopped and the tared thimble is weighed to determine the weight of fines. The percent of fines is calculated.

$$\% \text{ fines} = \frac{\text{g. of fines collected}}{\text{g. of catalyst charged}} \times 100$$

$$\text{Attrition Index (A.I.)} = \frac{\% \text{ fines from test catalyst}}{\% \text{ fines from commercial catalyst}}$$

EXAMPLE 1

A paste was formed by mixing the following components together in a beaker: 100 g. of $V_2O_5$, 72 g. of 42.9% $ZrO(CH_3COO)_2$, 152 g. of 85% $H_3PO_4$ and 14 g. of ethylene glycol. The paste was mixed with a spatula to obtain homogeneity. The paste was then transferred to a dish and dried at 135°C. overnight. The glycol reduces the $V^{+5}$ to $V^{+4}$ during mixing and drying. The dry cake was ground and sieved to −60 + 270 mesh.

100 cc. of the sieved product was activated overnight in a fluid bed reactor at 450°C. with a flow of air and n-butane. The air to n-butane ratio was 1000/10. After activation, the catalyst was cooled to 410°C. At this temperature, a feed mixture air /n-butane was passed through the bed at a rate of 1000 cc. air/40 cc. of n-butane per minute. This gave the following results:

| Conversion of n-$C_4$ | MA, wt. % | Selectivity |
|---|---|---|
| 63.2 | 68.1 | 61 |

The attrition index for this preparation was 1.0.

EXAMPLE 2

Using the procedure of Example 1, a catalyst having a V/P/Zr atomic ratio of 1/1.2/0.13 was prepared using 20 g. of propylene glycol in place of 14 g. of ethylene glycol per 100 g. of $V_2O_5$.

As described in Example 1, 100 cc. of sieved catalyst was activated overnight in a fluid bed reactor and then a feed mixture of 1000 cc. air/40 cc. of n-butane per minute was passed through the reactor at 405°C. This gave the following results:

| Conversion of n-$C_4$ | MA, wt. % | Selectivity |
|---|---|---|
| 62.4 | 58.5 | 60 |

EXAMPLE 3

Using the procedure of Example 1, a catalyst having a V/P atomic ratio of 1/1.2 and containing no Zr was prepared using 15 g. of ethylene glycol per 100 g. of $V_2O_5$.

As described in Example 1, 100 cc. of sieved catalyst was activated overnight in a fluid bed reactor and then a feed mixture of 1000 cc. air/40 cc. of n-butane per minute was passed through the reactor at 450°C. This gave the following results:

| Conversion of n-$C_4$ | MA, wt. % | Selectivity |
|---|---|---|
| 54.7 | 54 | 60 |

EXAMPLE 4

Using the procedure of Example 1, a catalyst having a V/P/Zr atomic ratio of 1/1.2/0.13 was prepared using 5 g. of sucrose per 100 g. of $V_2O_5$, instead of ethylene glycol.

As described in Example 1, 100 cc. of sieved catalyst was activated overnight in a fluid bed reactor and then a feed mixture of 1000 cc. air/40 cc. of n-butane per minute was passed through the reactor at 410°C. This gave the following results:

| Conversion of n-$C_4$ | MA, wt. % | Selectivity |
|---|---|---|
| 62.8 | 61.1 | 62 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for preparing a vanadium-phosphorus-oxygen complex catalyst that comprises mixing: (1) a vanadium compound, an organic reducing agent, and phosphoric acid or a compound which hydrolyzes to phosphoric acid; or (2) a vanadium compound, an organic reducing agent, a promoter metal compound, and phosphoric acid or a compound which hydrolyzes to phosphoric acid; to form a paste, drying the paste and calcining the resulting dried paste; thereby producing a catalyst complex consisting essentially of (1) vanadium-phosphorus-oxygen or (2) promoted vanadium-phosphorus-oxygen.

2. The method of claim 1, wherein said reducing agent is an organic hydroxy- or oxo-compound.

3. The method of claim 1, wherein said reducing agent is ethylene glycol.

4. The method of claim 1, wherein said reducing agent is propylene glycol.

5. The method of claim 1, wherein said reducing agent is sucrose.

6. The method of claim 1, wherein there is mixed $V_2O_5$, ethylene glycol, and phosphoric acid.

7. The method of claim 1, wherein there is mixed $V_2O_5$; ethylene glycol, propylene glycol, or sucrose; zirconyl acetate; and phosphoric acid.

8. The method of claim 1, wherein the atomic ratio of phosphorus-vanadium is between about 0.5 and about 2 and the atomic ratio of promoter metal/vanadium is between about 0.0025 and about one.

* * * * *

UNITED STATES PATENT AND TRADEMARK OFFICE
CERTIFICATE OF CORRECTION

PATENT NO. : 3,975,300
DATED : August 17, 1976
INVENTOR(S) : George T. Burress

It is certified that error appears in the above-identified patent and that said Letters Patent are hereby corrected as shown below:

| | |
|---|---|
| Col. 1, line 31 | "261.030" should be —261,030—. |
| Col. 1, line 51 | "present a corrosivity" should be —present a high corrosivity—. |
| Col. 2, line 37 | "VOCL$_3$" should be —VOCl$_3$—. |
| Col. 3, line 8 | "heodymium" should be —neodymium—. |
| Col. 3, line 57 | "4 to 6" should be —4 and 6—. |
| Col. 6, line 65 | "phosphorus-vanadium" should be —phosphorus/vanadium—. |

Signed and Sealed this

Fourth Day of January 1977

[SEAL]

Attest:

RUTH C. MASON
Attesting Officer

C. MARSHALL DANN
Commissioner of Patents and Trademarks